United States Patent
Bensaoula et al.

(10) Patent No.: US 8,328,785 B2
(45) Date of Patent: Dec. 11, 2012

(54) USE OF NANOPARTICLES IN THE PHOTODYNAMIC TREATMENT OF TUMORS

(75) Inventors: Abdelhak Bensaoula, Houston, TX (US); John Christopher Boney, Pearland, TX (US); A. Sam Beddar, Houston, TX (US); Tina Marie Briere, Houston, TX (US); Sunil Krishnan, Houston, TX (US); Andrew K. Lee, Houston, TX (US)

(73) Assignees: The University of Houston System, Houston, TX (US); Board of Regents, The University of Texas System, Austin, TX (US)

( * ) Notice: Subject to any disclaimer, the term of this patent is extended or adjusted under 35 U.S.C. 154(b) by 807 days.

(21) Appl. No.: 11/856,505

(22) Filed: Sep. 17, 2007

(65) Prior Publication Data

US 2008/0139993 A1 Jun. 12, 2008

Related U.S. Application Data (60) Provisional application No. 60/845,400, filed on Sep. 18, 2006.

(51) Int. Cl.
*A61M 31/00* (2006.01)

(52) U.S. Cl. .................................. 604/500; 250/492.3
(58) Field of Classification Search .................. 604/20, 604/890.1, 19, 500, 891.1; 128/897, 898, 128/899; 607/88–94; 250/251, 492.3, 493.1, 250/526
See application file for complete search history.

(56) References Cited

U.S. PATENT DOCUMENTS

| | | | | |
|---|---|---|---|---|
| 6,036,631 A | * | 3/2000 | McGrath et al. | 600/3 |
| 2001/0051760 A1 | * | 12/2001 | Hofstetter et al. | 600/2 |
| 2002/0127224 A1 | * | 9/2002 | Chen | 424/130.1 |
| 2007/0218049 A1 | * | 9/2007 | Chen et al. | 424/130.1 |

* cited by examiner

*Primary Examiner* — Kevin C Sirmons
*Assistant Examiner* — Kami A Bosworth
(74) *Attorney, Agent, or Firm* — Robert W Strozier (57) ABSTRACT

A method for generating light intensity inside a tumor to aid in the treatment of diseases such as cancer is disclosed. The light is generated inside the body to perform a modified photodynamic therapy treatment (PDT) that allows treatment of body regions that are inaccessible by normal PDT procedures. In addition, the use of two spatially and temporally coincident treatment modalities, i.e. radiation and PDT, have the potential for significant biological synergy in the tumor.

12 Claims, 6 Drawing Sheets

USE OF NANOPARTICLES IN THE PHOTODYNAMIC TREATMENT OF TUMORS

RELATED APPLICATIONS

The application claims priority to U.S. Patent Application Ser. No. 60/845,400, filed 18 Sep. 2006.

BACKGROUND OF THE INVENTION

1. Field of the Invention

The present invention relates generally to a method for generating photons for photo-dynamic therapy inside an animal including an human.

More particularly, the present invention relates to a method for generating photons for photo-dynamic therapy inside an animal including an human, where the method includes the step of placing nano-particles in a tissue site, where the nano-particles are capable of converting a portion of energized electrons created by irradiating the tissue site to photons within the tissue site, extending the use of photo-dynamic therapy (PDT) to deep tissues and organs.

2. Description of the Related Art

Radiation treatments for tumors, especially cancerous tumors, can have long term negative impacts on a patient, due to cell damage in non-tumor regions arising from the high levels of radiation used, including greatly reducing the patient's quality of life. While, using a lower-than-normal radiation dose for the treatment lessens the effectiveness of the treatment.

Photo-dynamic therapy (PDT) is a light-based tumor treatment which is currently used in medical practice. However, the light used in traditional PDT techniques is generated external to the body and brought to the tumor region which is inside the body by means of light pipes or optical fibers, limiting such procedures to certain areas of the body (e.g., skin, esophagus, lung, bladder).

Although PDT techniques are available, their limitations both in light focusing and control and light placement make them less robust than other techniques. Thus, there is a need in the art for improved PDT techniques that lessen adverse treatment impacts on the patient, that allow reduced radiation treatments and that expand the reach of the techniques to body regions that are inaccessible by normal photo-dynamic procedures.

SUMMARY OF THE INVENTION

The present invention provides a method of photo-dynamically treating a target site of an animal including an human, such as a tumor or other cancerous tissue site, including the step of administering an amount of nano-particles to the animal. Once the nano-particles have been administered, the tissue site is treated with radiation, where some or all of the nano-particles absorb a portion of energized electrons created by the radiation and convert a portion of the absorbed energy into photons within the site. A portion of the photons are absorbed by photosensitizers that activate oxygen in the site to produce reactive oxygen species that in conjunction with the radiation result in a reduction of a tumor size within the tissue site or death of some or all of the cancer cells within the tissue site.

The present invention also provides a method of photo-dynamically treating a target site of an animal including an human, such as a tumor or other cancerous tissue site, including the steps of administering an amount of nano-particles to the animal. After administration of the nano-particles, the tissue site is irradiated with radiation of sufficient energy to generate excited electrons in the site, wherein the nano-particles absorb a portion of the energy associated with the excited or energized electrons and convert a portion of the absorbed energy into photons within the site. A portion of the photons are absorbed by photosensitizers that activate oxygen in the site to produce reactive oxygen species that in conjunction with the radiation result in a reduce of the tumor size within the site or the death of some or all of the cancer cells within the tissue site.

The present invention also provides a method of photo-dynamically treating a target site of an animal including an human, such as a tumor or other cancerous tissue site, including the steps of administering an amount of nano-particles to the animal. After administration of the nano-particles, the tissue site is irradiated with radiation of sufficient energy to generate excited electrons within the site and irradiating the tissue site with additional radiation of the same or different energy, wherein the nano-particles absorb a portion of energy associated with the excited or energized electrons and convert a portion of the absorbed energy into photons within the site. The site also has administered to it radiation from a second radiation source that also generates excited electrons, a portion of the energy is absorbed by the nano-particles and a portion thereof into additional photons. A portion of the photons are absorbed by photosensitizers that activate oxygen in the site to produce reactive oxygen species and coupled with the radiations associated with the two sources result in a reduce of the tumor size within the site or the death of some or all of the cancer cells within the tissue site. The two radiations are a brachy type and an external radiation type.

The present invention provides a nano-particle composition including an effective amount of nano-particles in a bio-acceptable carrier, where the nano-particles are capable of absorbing a portion of energy associated with excited or energized electrons formed by exposing a site including the nano-particles with radiation having a sufficient energy to generate excited electrons within the site, where the nano-particles absorb a portion of energy of the excited or energized electrons and convert a portion of the absorbed energy into photons within the site. These photons can then be used to activate photosensitizers also in the site to produce reaction oxygen species that in conduction with the radiation result in a reduce of the tumor size within the site or the death of some or all of the cancer cells within the tissue site.

The present invention also provides structures including the nano-particles, where the nano-particles are used to generate photons wirelessly within structures, where the structures can be transparent, translucent, partially opaque or opaque. The light emitting nano-particles are especially well suited for translucent, partially opaque and opaque structures where standard photolytic means would not represent a viable method for introducing photons into the structures. The term partially opaque means that the structure has opaque part and non-opaque parts or that the structure is sufficiently opaque that external photolytic methods are incapable of efficiently producing sufficient photons to activate a photo-activatable device with in the structure. The nano-particles can be part of a light powered device within the structure, where the devices can be electromechanical devices for performing a task with in the structure or communication devices for receiving and/or transmitting data depending on the communication devices. The present invention can also include method using the generated photons to probe characteristics of structures in which the nano-particles are embedded, injected or inserted, to power embedded devices or to receive and/or transmit information or to collection and transmits collected information, where the devices are only active when the nano-particles are activated by external or internal irradiation.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

The inventors have found that photo-dynamic treatment can be extended to deep tissue sites by administering an effective amount of nano-particles to the tissue site, where the nano-particles are capable of absorbing energy from excited electrons produced by exposing the site to radiation and converting a portion of the excited electron energy into photons within the site, a portion of which a photosensitizer producing reactive oxygen species that result in a reduction of the tumor size or the death of some or all of the cancer cells within the tissue site.

The present invention is a method for efficient treatment of tissue sites such as tumors (benign or cancerous) or other cancerous tissues, by generating light inside the tumor to perform photo-dynamic treatment (PDT). This allows treatment of body regions that are inaccessible for normal PDT procedures. In addition, by using two spatially and temporally coincident treatment modalities (radiation and PDT), the treatment allows for significant biological synergy in the tumor.

One embodiment of the method includes the use of engineered nano-particles in combination with photo-sensitizer molecules and a radiation source that is generated either externally or internally to the body. The engineered material converts radiation used during cancer treatments (e.g., in the form of either external beams or implanted radioactive seeds) into light that can be used to perform photo-dynamic therapy.

In addition to generating light inside the body at a target tissue site through radiation conversion, this method also enables two simultaneous treatments from a single source. Simultaneous treatments have the advantage of increasing the effectiveness of the combined treatment relative to either of the single treatments alone and the advantage of eliminating additional patient discomfort and inconvenience of undergoing two distinct treatments. This method benefits tumor patients through increased treatment options, enhanced treatment effectiveness, and improved quality of life following treatment.

To describe the invention in detail and maximize the understanding of the invention, one example (the treatment of prostate cancer) is discussed. This example of treating prostrate cancer is for illustrative purposes only and is not intended to limit the scope of the method or the applications of the present invention.

Radiation-based therapy is an approved treatment for early stage prostate cancer that utilizes either externally generated beams of radiation focused on the prostate or a transperineal interstitial implantation technique (brachytherapy) to deposit radioactive seeds (typically either $^{125}$I or $^{103}$Pd) within the prostate. The biochemical relapse-free survival times of radiation treatments are comparable to prostate removal (prostatectomy). A combination of external beam and brachytherapy treatments are often used for more advanced disease states.

One embodiment of the present invention is to modify standard radiation treatments with the addition of concurrent photo-dynamic therapy (PDT). PDT is a clinically approved and rapidly evolving cancer treatment regimen. PDT traditionally involves administration of a photo-sensitizer that preferentially accumulates within a tumor. Following illumination of the tumor with light of an appropriate wavelength, in the presence of molecular oxygen, reactive oxygen species are produced which, in turn, damage cellular structures containing the photo-sensitizer. The effects are localized to the vicinity of the tumor and within a few millimeters of the light source, which minimizes systemic and normal tissue toxicity.

In PDT, a narrow wavelength band of light is used to activate the photosensitizer. This light is typically from a laser or light emitting diode source and is often in the red portion of the spectrum ($\lambda > 600$ nm) due to the body's rapid absorption of shorter visible and UV wavelengths. Even red light is attenuated to some degree by the body, which limits the depth of treatment to 1 to 2 cm at most. The prostate is not readily accessible for laser illumination, and thus attempts at clinical application of PDT for the prostate have been limited. The energy deposited in the body's tissues from radiation sources, however, can be used to generate photons of the appropriate wavelength range for the photo-sensitizer being used. The conversion requires the use of an intermediary material that must also be present in the tumor region. In addition, the fact that the intermediary material is present in the tumor region means that wavelengths of light shorter than red can potentially be used since the body's absorption would be less of an issue.

One embodiment uses nano-particles and especially semiconductor nano-particles, as the intermediary, which can be delivered to the tumor in several different methods, including insertion in pellet form along with brachytherapy radioactive sources, localized injection, or dispersal into the bloodstream. It is well known that the high-energy photons used in external beam therapy or those created by the decay of radioactive sources used in brachytherapy ultimately release their energy into the body in the form of energetic electrons. In one embodiment, these energetic electrons are used to form 630-nm (~2 eV) photons through an interaction between the energetic electrons and the semiconductor nano-particles. This is a cathodoluminescence process and results in the emission of photons from the nano-particles that correspond to the semiconductor bandgap. The photon energy of 2 eV is appropriate for use with PHOTOFRIN® (a registered trademark of Axcan Pharma Inc., Birmingham, Ala.) to date the only photo-sensitizer for PDT approved by the FDA.

Other photosensitizers at longer (>630 nm) and shorter (<630 nm) wavelengths are under development for conventional PDT by many researchers. Such photosensitizers would also be compatible with semiconductor nanoparticles as the intermediary converter. Additionally, some existing photosensitizers, such as PHOTOFRIN® (a registered trademark of Axcan Pharma Inc., Birmingham, Ala.), have stronger (primary) absorption bands at wavelengths less than those used for existing PDT treatments. Such absorption bands are not used due to the body's absorption of those wavelengths from external sources. In these cases treatments could be improved with the use of semiconductor nano-particles to generate the shorter wavelengths directly in the tumor region to increase treatment efficiency and reduce the effect of the body's absorption of the shorter wavelengths.

The use of PDT with radiation therapy combines two modalities with established anti-tumor activity for additive and/or synergistic tumoricidal effect that can permit greater tumor control rates with reduced toxicity.

In the prostate embodiment, the method in its most basic form involves the capture or absorption of a part of the energy released into a tissue site by an external radiation beam or a radiation generated via radioactive decay of a radioactive source implanted in the tissue site during brachytherapy. The captured or absorbed energy is then converted it to photons of an appropriate energy range to activate photo-dynamic therapy, i.e., to activate a given photo-sensitizer. This treatment requires three components:

(1) a source of radiation—e.g., 0.01 to 50 MeV photons (gamma rays or x-rays), $^{125}$I seed, $^{103}$Pd seed, or another energetic radiation source;

(2) a photosensitizer, such as Photofrin, present in the target tissue such as a tumor or tumor region; and (3) an appropriate nano-particle having a desire bandgap also present in the target tissue such as a tumor or tumor region, to convert a portion of the energetic electrons produced by the radiation source into photons that can be absorbed by the photosensitizer.

The concept relies on producing enough photon flux through cathodoluminescence conversion in the tumor area to result in tumor size reduction, tumor cell death or tumor destruction.

To illustrate the concept, the total photon dose in conventional PDT is compared with the expected photon dose from the cathodoluminescence process of the present invention in conjunction with brachytherapy treatment.

In this illustration, the prostate is assumed to have a volume between about 30 cm$^3$ and about 50 cm$^3$ and an average cross-sectional area of about 14 cm$^2$. The number of photons used in typical PDT therapy of accessible tumors (such as tumors in the head and neck, bladder, and esophageal) is calculated. A fluence between about 20 and about 400 J/cm$^2$ at 630-nm (~2 eV photon energy) is typically used for Photofrin in these cases. This is easily converted to the total number of photons used in the therapy:

$$20 \text{ J/cm}^2 = (20 \text{ J/cm}^2) * (1 \text{ eV}/1.6 \times 10^{-19} \text{J}) * \qquad (1)$$
$$(1 \text{ photon}/2 \text{ eV}) * (14 \text{ cm}^2)$$
$$= 8.8 \times 10^{20} \text{ photons}$$

$$400 \text{ J/cm}^2 = (400 \text{ J/cm}^2) * (1 \text{ eV}/1.6 \times 10^{-19} \text{J}) * \qquad (2)$$
$$(1 \text{ photon}/2 \text{ eV}) * (14 \text{ cm}^2)$$
$$= 1.8 \times 10^{22} \text{ photons}$$

A calculation of the 630-nm photon dose from the therapy of the present invention begins by assuming that a typical radiation dose used for the treatment of prostate cancer by brachytherapy is about 150 Gy (a more typical dose being 70 Gy). The same prostate dimensions as above are used as a water model to derive:

$$150 \text{ Gy} = 150 \text{ J/kg} * (1 \text{ kg}/1000 \text{ cm}^3) * \qquad (3)$$
$$(40 \text{ cm}^3) * (1 \text{ eV}/1.6 \times 10^{-19} \text{J})$$
$$= 3.75 \times 10^{19} \text{ eV per treatment}$$

To convert this energy to photons usable for PDT, the following is taken into account along with several assumptions and approximations:

(1) The disintegrations occur uniformly in the 4 cm diameter that is the prostate model.

(2) $^{125}$I and $^{103}$Pd emit primarily x-rays in the range of 27-36 keV and 20-23 keV, respectively. For photon energies less than ~50 keV, the primary energy absorbed is through photoelectric events. In a photoelectric process, a large part of the energy of the incoming high-energy photon is utilized to overcome an inner shell or core electron binding energy and the excess energy is converted to kinetic energy of the ejected inner shell electron. For 20 to 36 keV photons, 80-94% of the energy lost to a water phantom will be in the form of photoelectrons. In this illustration, an 85% loss is assumed.

(3) The amount of energy needed to create a photon in a semiconductor or other nano-particles having a desired bandgap in a cathodoluminescence process is 3* bandgap energy, which in this case is 3 times the energy of the photon produced (630 nm is 2 eV*3=6 eV/photon).

(4) A single injection of Photofrin is done, which is active during two-thirds of the mean life of the radioactive source [$\tau_{1/2}(^{125}$I$)$=60 days].

$$150 \text{ Gy} = (3.75 \times 10^{19} \text{ eV}) * (0.85) * (1 \text{ photon}/6 \text{ eV}) * 0.67 \qquad (4)$$
$$= 3.5 \times 10^{18} \text{ photons per treatment}$$

There are few semiconducting materials in bulk form that are both non-toxic and have a band gap at 2.0 eV. However, quantum size effects can be used to alter the bandgap of a semiconductor. In reducing size from "bulk" down to a nanometer scale, the bandgap energy of a semiconductor increases due to quantum mechanical confinement. The smaller a particle is made (increasing electron confinement), the larger the increase in its effective bandgap energy. Potential nano-engineered particles have been identified for application to PDT. These include, without limitation, CdSe/ZnS, CdTe/CdS, and InP core and core/shell nano-particles with sizes ranging from 1.5 to 4.5 nm. However, any nano-particle structure having these compositions and sizes are meant by way of example and are not meant to limit the scope of the invention.

The calculations concerning the total number of photons produced by the nano-particles assumed that they covered 100% of the prostate volume. Although a coverage from 5% to 10% of the prostate volume may be expected, there is an additional potential benefit to the use of semiconductor nano-particles in the tumor region, and that is the enhancement of the radiation dose. Most of the nano-particles that could be used in the PDT process have densities between 4.8-5.9 g/cm$^3$. Their corresponding $Z_{avg}$ is on the order of 45 (for CdSe $Z_{avg}$=43.5, CdTe $Z_{avg}$=50.2, Inp $Z_{avg}$=45.5), compared to that of water and soft tissue ($Z_{avg}$~7.4-7.5). Because the mass attenuation coefficient for a photoelectric process scales is $Z^3$ to $Z^{3.8}$, an enhancement ratio of 200-900 is possible in the vicinity of a nano-particle.

Although a similar comparison calculation for external beam radiation prostate treatments is difficult to perform, the following is known:
(1) At energies of 1 MeV and above, the primary energy absorbed is either through Compton scattering or pair production, with Compton dominating at low MeVs and pair production increasing in importance with increasing energy.
(2) Both Compton and pair processes create energetic electrons, but these electrons have a wide range of possible energies (unlike the electrons from the radiotherapy seed sources) which is why a simple calculation is not possible.
(3) All radiation cancer treatments are based on the radiation dose given in Grays (Gy) which is the amount of energy absorbed (joules J) per body mass (kilograms kg). Therefore, using the previous calculations of 150 Gy=3.5×10$^{18}$ photons in brachytherapy, it is estimated that for external beam therapy approximately 2.8×10$^{16}$ photons per Gray of treatment can be generated assuming 68% energy transfer to Compton electrons (0.68 is a mean fractional incident energy given to a Compton recoil electron at 10 MeV).
(4) Most external beam therapies use tens of Gray for prostate treatment, which is then on the order of 1×10$^{17}$ photons per treatment.

In another embodiment, the nano-particles are treated with the photosensitizer so that the photosensitizer is associated with the nano-particles either covalently or contained in a coating surrounding the nano-particles provided the coating does not adversely affect cathodoluminescence conversion of higher energy electrons into photons of an energy sufficient to energize the photosensitizers.

The cancer or tumor include, without limitation, carcinomas, melanomas, lymphomas, plasmocytoma, sarcoma, glioma, thymoma, brain tumor, myeloma, leukemia, or a tumor of pharynx, bones, joints, soft tissue, skin, breast, eye, orbit, the nervous system, endocrine system, urinary system, genital system, respiratory system, digestive system, oral cavity and/or combinations thereof.

DETAILED DESCRIPTION OF THE DRAWINGS

Figure 1:
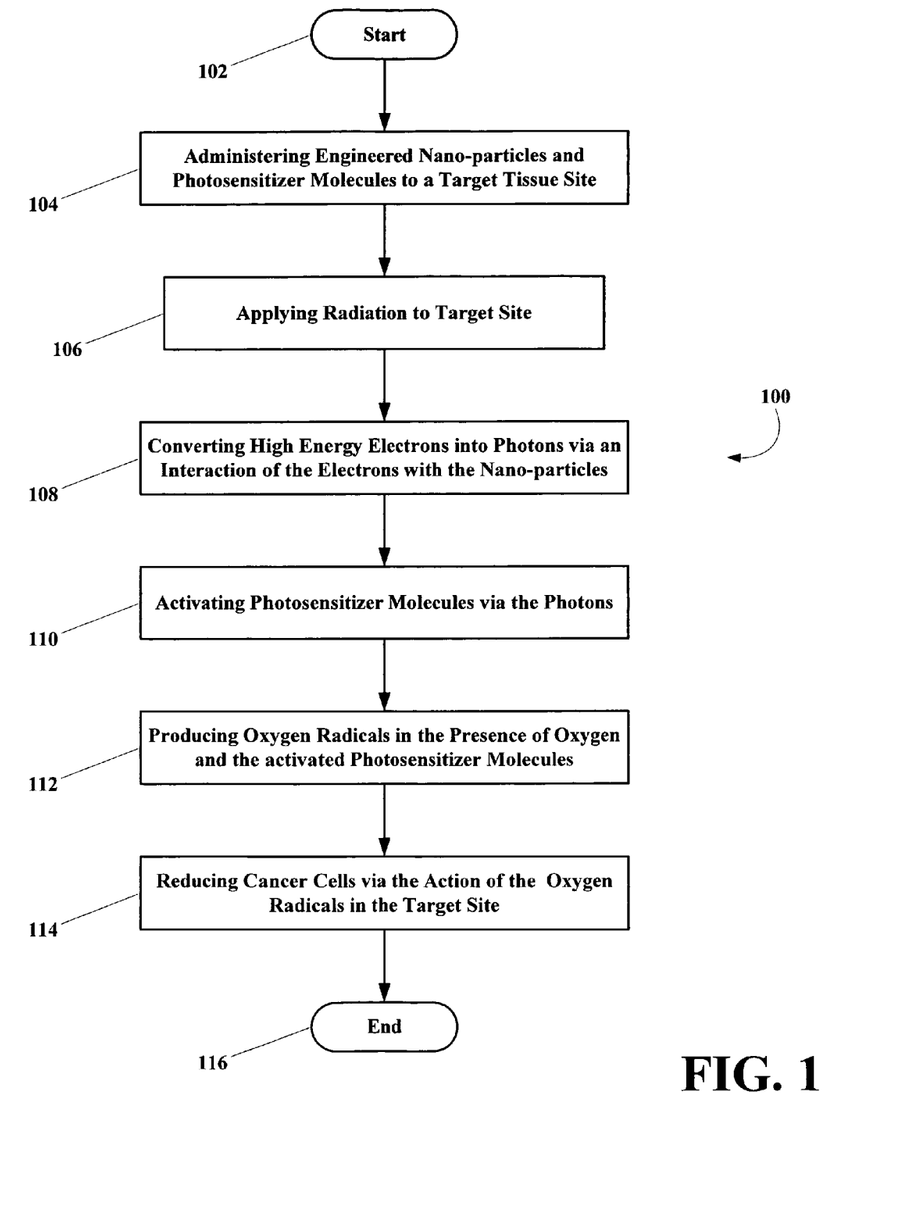
FIG. 1 depicts a flow chart of a generalized embodiment of a method of the invention for radiation induced photo-dynamic treatment or radiation and radiation induced photo-dynamic treatment of a tissue site.

Referring now to FIG. 1, a flow chart, generally 100, illustrates of a generalized embodiment of a method of the present invention. The method begins with a start step 102. The start step 102 is simply a flow chart convenience in actuality the method actually begins with the first step involving the treatment. However, the start step 102 does mean that the medical team has assembly and has the necessary amount of nano-particles having a desired bandgap for converting energized electronic into photons having an energy sufficient to excite corresponding photosensitizer molecules. Once the team and materials are ready, the nano-particles and photosensitizer molecules are administered to a target tissue site in administering step 104. The administering step 104 can be any known or yet to be invented administering step that is capable of localizing an effective amount of the nano-particles and the photosensitizer in the target site, e.g., injection into the blood stream with affinity agents to aid in localization, direct injection into the tissue site and/or surrounding region, direct profusion into the tissue site and/or surrounding, or any other administering step that is capable of localizing an effective amount of both the nano-particles and the photosensitizer in the target site. The tissue site can be a tumor and/or the tumor and surrounding tissue, a non-tumor cancerous growth or any other tissue site include cells that require eradication via radiation or oxygen radicals induced by light activated photosensitizers. After the nano-particles and photosensitizer molecules (whether individually, collectively, or in an associated format) is administered and effective amount of the nano-particles and photosensitizer molecules are present in the tissue site, radiation is applied to the tissue site in an applying radiation step 106. As the radiation is applied to the tissue site during the applying radiation step 106, a portion of the radiation produces energized electrons such as photoelectrons, Compton electrons, or the like, are absorbed by the nano-particles and converted into photons having a desired frequency range in a converting step 108. After conversion, the photon are absorbed by the photosensitizer molecules forming activated photosensitizer molecules in an activating photosensitizer step 110. The activated photosensitizer molecules in the presence of oxygen in the tissue site produces oxygen radicals in a producing oxygen radicals step 112. The produced oxygen radicals then interact with the cells of the tissue site resulting in cell death or a reduction or elimination of a tumor in a reducing cancer cells step 114. After a desired duration of applying radiation, the treatment is stopped in a stop step 116.

Figure 2:
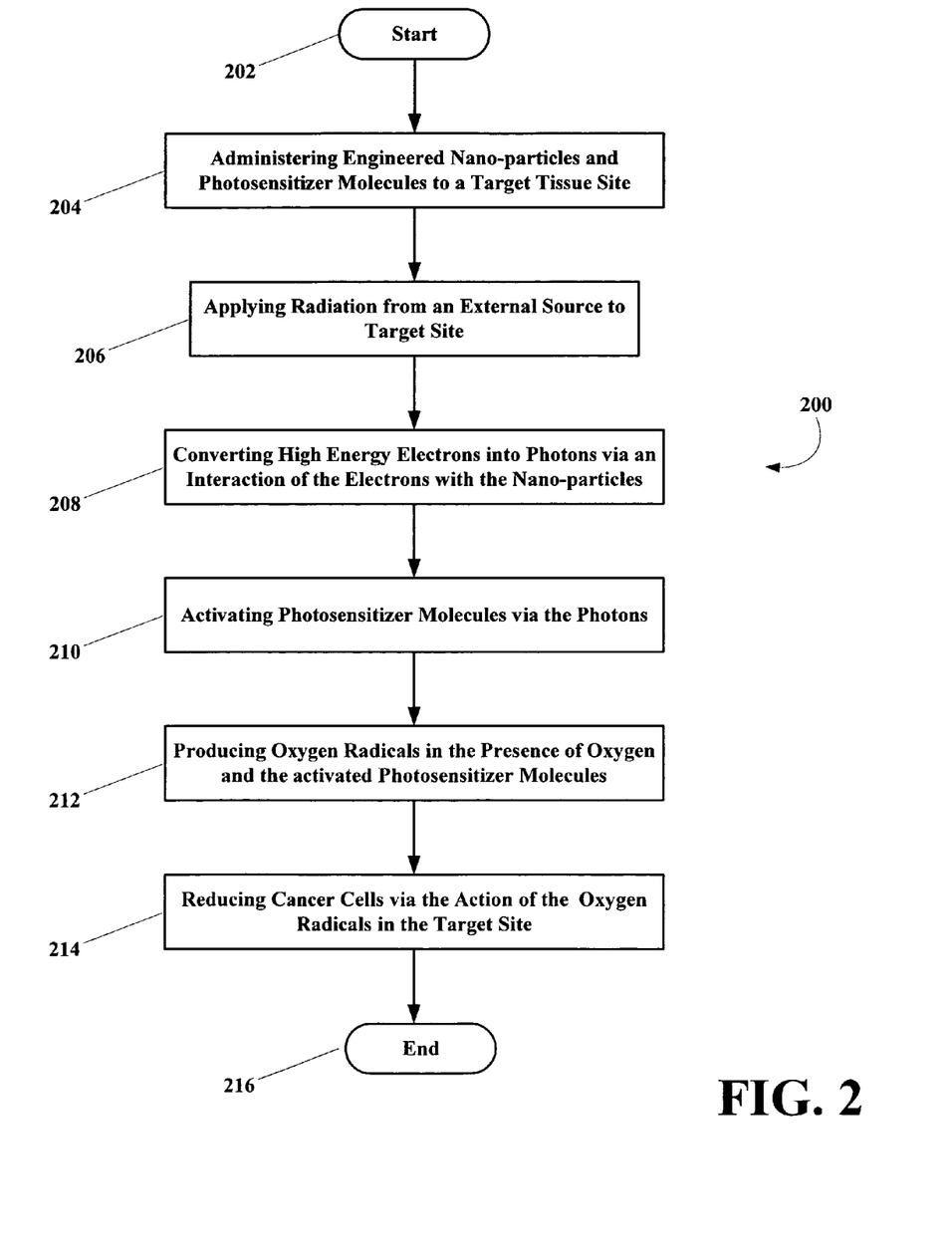
FIG. 2 depicts a flow chart of an irradiation embodiment of a method of the invention for radiation induced photo-dynamic treatment or radiation and radiation induced photo-dynamic treatment of a tissue site.

Referring now to FIG. 2, a flow chart, generally 200, illustrates of an irradiation embodiment of a method of the present invention. The method begins with a start step 202. The start step 202 is simply a flowchart convenience in actuality the method actually begins with the first step involving the treatment. However, the start step 202 does mean that the medical team has assembly and has the necessary amount of nano-particles having a desired bandgap for converting energized electronic into photons having an energy sufficient to excite corresponding photosensitizer molecules. Once the team and materials are ready, the nano-particles and photosensitizer molecules are administered to a target tissue site in administering step 204. The administering step 204 can be any known or yet to be invented administering step that is capable of localizing an effective amount of the nano-particles and the photosensitizer in the target site, e.g., injection into the blood stream with affinity agents to aid in localization, direct injection into the tissue site and/or surrounding region, direct profusion into the tissue site and/or surrounding, or any other administering step that is capable of localizing an effective amount of both the nano-particles and the photosensitizer in the target site. The tissue site can be a tumor and/or the tumor and surrounding tissue, a non-tumor cancerous growth or any other tissue site include cells that require eradication via radiation or oxygen radicals induced by light activated photosensitizers. After the nano-particles and photosensitizer molecules (whether individually, collectively, or in an associated format) is administered and effective amount of the nano-particles and photosensitizer molecules are present in the tissue site, the tissue site is irradiated with radiation from a radiation sources such as, but are not limited to, gamma ray or X-rays of 0.02 to 50 MeV, or the like, in an irradiation step 206. As the radiation is applied to the tissue site during the applying radiation step 206, a portion of the radiation produces energized electrons such as photoelectrons, Compton electrons, or the like, are absorbed by the nano-particles and converted into photons having a desired frequency range in a converting step 208. After conversion, the photon are absorbed by the photosensitizer molecules forming activated photo sensitizer molecules in an activating photosensitizer step 210. The activated photosensitizer molecules in the presence of oxygen in the tissue site produces oxygen radicals in a producing oxygen radicals step 212. The produced oxygen radicals then interact with the cells of the tissue site resulting in cell death or a reduction or elimination of a tumor in a reducing cancer cells step 214. After a desired duration of applying radiation, the treatment is stopped in a stop step 216.

Figure 3:
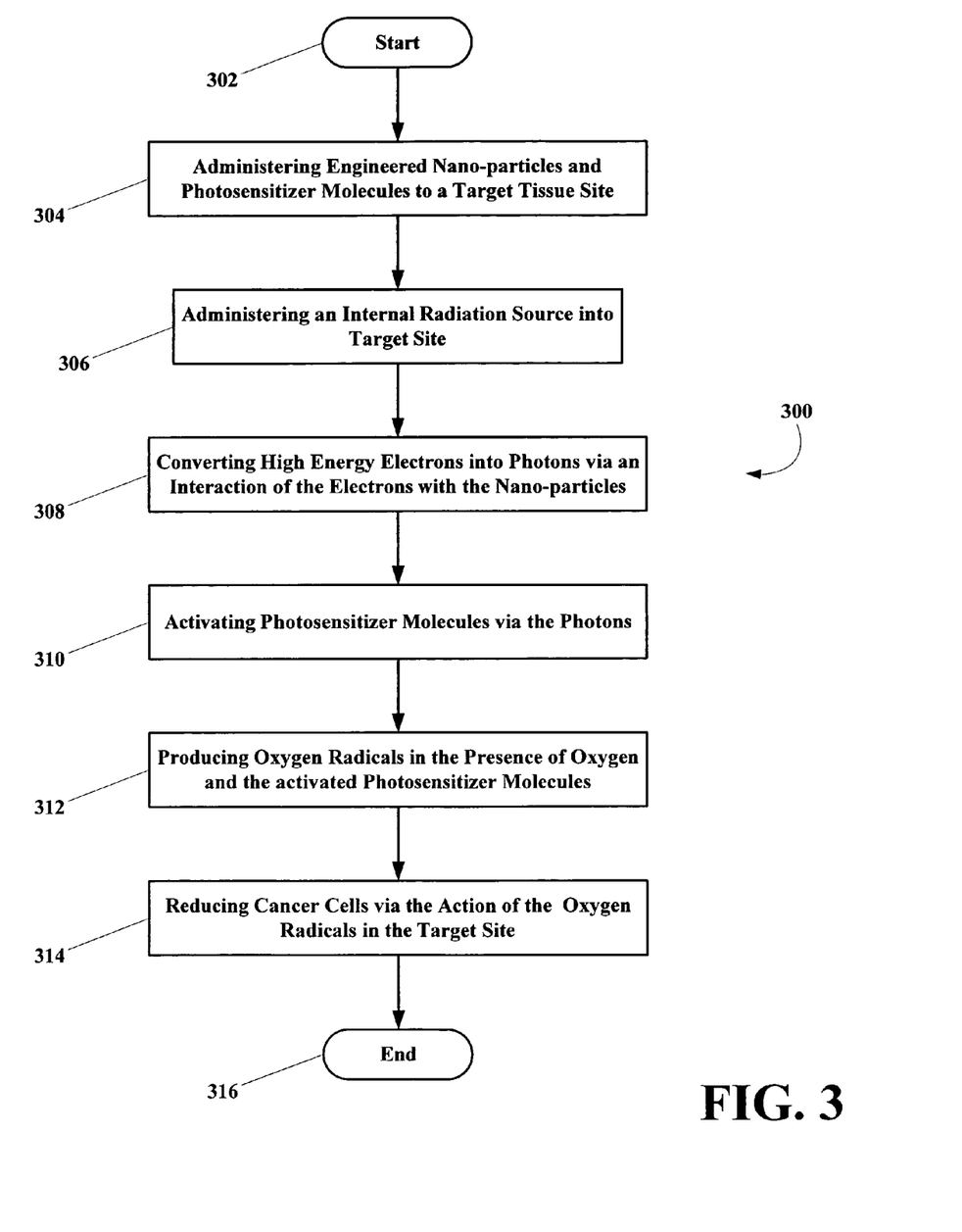
FIG. 3 depicts a flow chart of a generalized implanted radio-seed radiation source embodiment of a method of the invention for radiation induced photo-dynamic treatment or radiation and radiation induced photo-dynamic treatment of a tissue site.

Referring now to FIG. 3, a flow chart, generally 300, illustrates of a generalized implanted radio-seed embodiment of a method of the present invention. The method begins with a start step 302. The start step 302 is simply a flow chart convenience in actuality the method actually begins with the first step involving the treatment. However, the start step 302 does mean that the medical team has assembly and has the necessary amount of nano-particles having a desired bandgap for converting energized electronic into photons having an energy sufficient to excite corresponding photosensitizer molecules. Once the team and materials are ready, the nano-particles and photosensitizer molecules are administered to a target tissue site in administering step 304. The administering step 304 can be any known or yet to be invented administering step that is capable of localizing an effective amount of the nano-particles and the photosensitizer in the target site, e.g., injection into the blood stream with affinity agents to aid in localization, direct injection into the tissue site and/or surrounding region, direct profusion into the tissue site and/or surrounding, or any other administering step that is capable of localizing an effective amount of both the nano-particles and the photosensitizer in the target site. The tissue site can be a tumor and/or the tumor and surrounding tissue, a non-tumor cancerous growth or any other tissue site include cells that require eradication via radiation or oxygen radicals induced by light activated photosensitizers. After the nano-particles and photosensitizer molecules (whether individually, collectively, or in an associated format) is administered and effective amount of the nano-particles and photosensitizer molecules are present in the tissue site, radiation is applied to the tissue site in an applying radiation step 306. As the radiation is applied to the tissue site during the applying radiation step 306, a portion of the radiation produces energized electrons such as photoelectrons, Compton electrons, or the like, are absorbed by the nano-particles and converted into photons having a desired frequency range in a converting step 308. After conversion, the photon are absorbed by the photosensitizer molecules forming activated photosensitizer molecules in an activating photosensitizer step 310. The activated photosensitizer molecules in the presence of oxygen in the tissue site produces oxygen radicals in a producing oxygen radicals step 312. The produced oxygen radicals then interact with the cells of the tissue site resulting in cell death or a reduction or elimination of a tumor in a reducing cancer cells step 314. After a desired duration of applying radiation, the treatment is stopped in a stop step 316.

Figure 4:
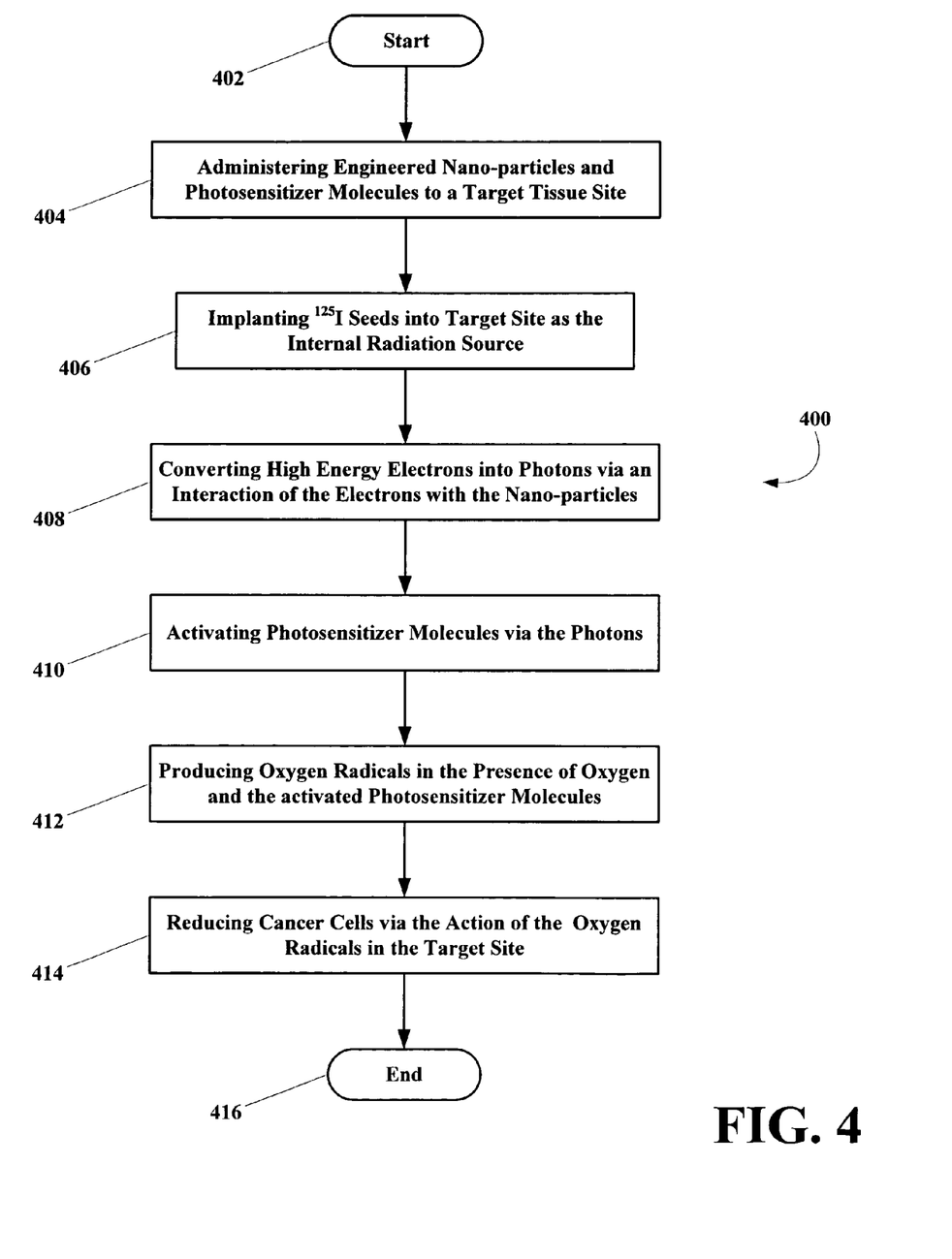
FIG. 4 depicts a flow chart of an implanted radio-seed radiation source embodiment of a method of the invention for radiation induced photo-dynamic treatment or radiation and radiation induced photo-dynamic treatment of a tissue site.

Referring now to FIG. 4, a flow chart, generally 400, illustrates of an implanted $^{125}$I radio-seed embodiment of a method of the present invention. The method begins with a start step 402. The start step 402 is simply a flow chart convenience in actuality the method actually begins with the first step involving the treatment. However, the start step 402 does mean that the medical team has assembly and has the necessary amount of nano-particles having a desired bandgap for converting energized electronic into photons having an energy sufficient to excite corresponding photosensitizer molecules. Once the team and materials are ready, the nano-particles and photosensitizer molecules are administered to a target tissue site in administering step 404. The administering step 404 can be any known or yet to be invented administering step that is capable of localizing an effective amount of the nano-particles and the photosensitizer in the target site, e.g., injection into the blood stream with affinity agents to aid in localization, direct injection into the tissue site and/or surrounding region, direct profusion into the tissue site and/or surrounding, or any other administering step that is capable of localizing an effective amount of both the nano-particles and the photosensitizer in the target site. The tissue site can be a tumor and/or the tumor and surrounding tissue, a non-tumor cancerous growth or any other tissue site include cells that require eradication via radiation or oxygen radicals induced by light activated photosensitizers. After the nano-particles and photosensitizer molecules (whether individually, collectively, or in an associated format) is administered and effective amount of the nano-particles and photosensitizer molecules are present in the tissue site, radiation is applied to the tissue site in an applying radiation step 406. As the radiation is applied to the tissue site during the applying radiation step 406, a portion of the radiation produces energized electrons such as photoelectrons, Compton electrons, or the like, are absorbed by the nano-particles and converted into photons having a desired frequency range in a converting step 408. After conversion, the photon are absorbed by the photosensitizer molecules forming activated photo sensitizer molecules in an activating photosensitizer step 410. The activated photosensitizer molecules in the presence of oxygen in the tissue site produces oxygen radicals in a producing oxygen radicals step 412. The produced oxygen radicals then interact with the cells of the tissue site resulting in cell death or a reduction or elimination of a tumor in a reducing cancer cells step 414. After a desired duration of applying radiation, the treatment is stopped in a stop step 416.

Figure 5:
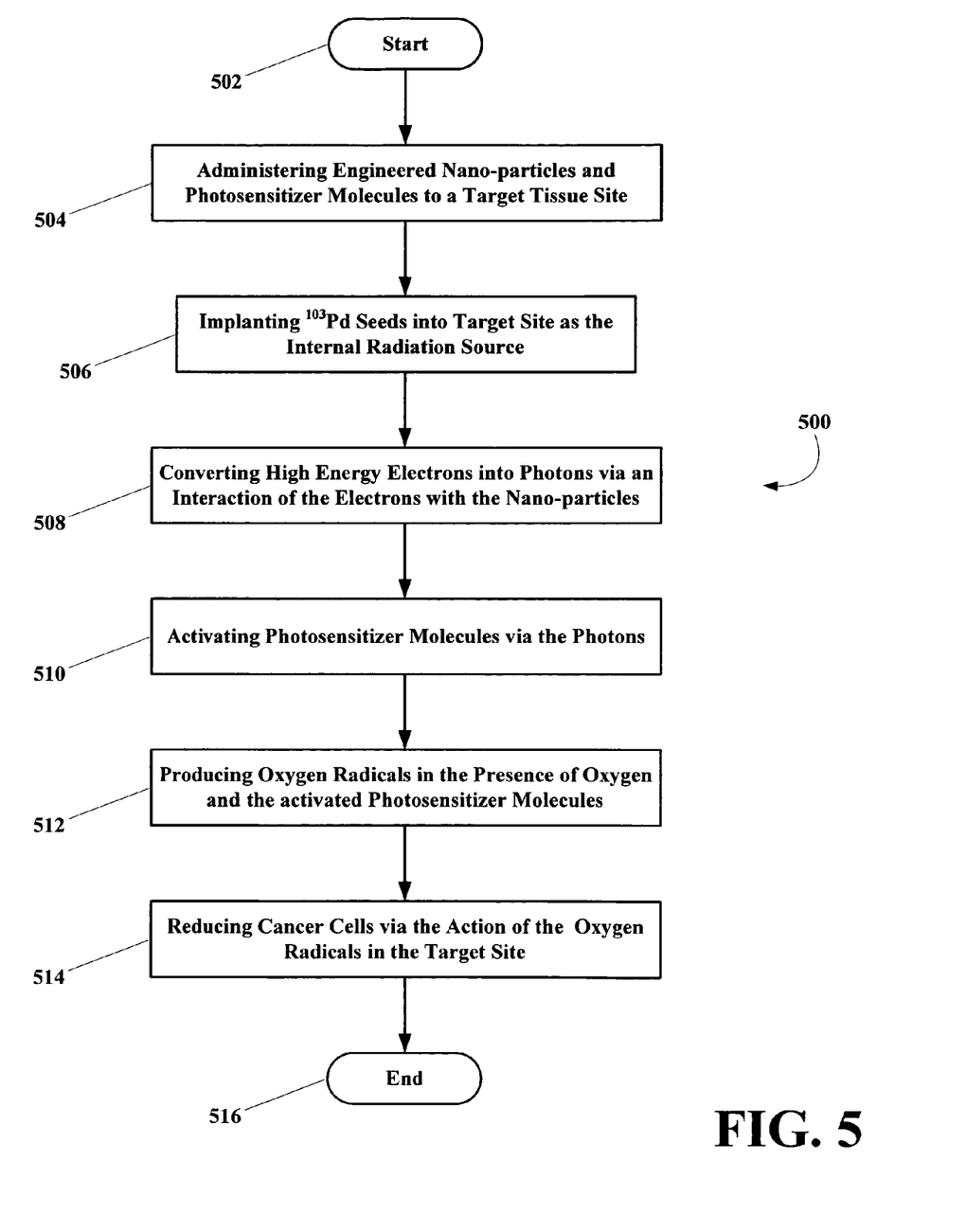
FIG. 5 depicts a flow chart of another implanted radio-seed radiation source embodiment of a method of the invention for radiation induced photo-dynamic treatment or radiation and radiation induced photo-dynamic treatment of a tissue site.

Referring now to FIG. 5, a flow chart, generally 500, illustrates of an implanted $^{103}$Pd radio-seed embodiment of a method of the present invention. The method begins with a start step 502. The start step 502 is simply a flow chart convenience in actuality the method actually begins with the first step involving the treatment. However, the start step 502 does mean that the medical team has assembly and has the necessary amount of nano-particles having a desired bandgap for converting energized electronic into photons having an energy sufficient to excite corresponding photosensitizer molecules. Once the team and materials are ready, the nano-particles and photosensitizer molecules are administered to a target tissue site in administering step 504. The administering step 504 can be any known or yet to be invented administering step that is capable of localizing an effective amount of the nano-particles and the photosensitizer in the target site, e.g., injection into the blood stream with affinity agents to aid in localization, direct injection into the tissue site and/or surrounding region, direct profusion into the tissue site and/or surrounding, or any other administering step that is capable of localizing an effective amount of both the nano-particles and the photosensitizer in the target site. The tissue site can be a tumor and/or the tumor and surrounding tissue, a non-tumor cancerous growth or any other tissue site include cells that require eradication via radiation or oxygen radicals induced by light activated photosensitizers. After the nano-particles and photosensitizer molecules (whether individually, collectively, or in an associated format) is administered and effective amount of the nano-particles and photosensitizer molecules are present in the tissue site, radiation is applied to the tissue site in an applying radiation step 506. As the radiation is applied to the tissue site during the applying radiation step 506, a portion of the radiation produces energized electrons such as photoelectrons, Compton electrons, or the like, are absorbed by the nano-particles and converted into photons having a desired frequency range in a converting step 508. After conversion, the photon are absorbed by the photosensitizer molecules forming activated photo sensitizer molecules in an activating photosensitizer step 510. The activated photosensitizer molecules in the presence of oxygen in the tissue site produces oxygen radicals in a producing oxygen radicals step 512. The produced oxygen radicals then interact with the cells of the tissue site resulting in cell death or a reduction or elimination of a tumor in a reducing cancer cells step 514. After a desired duration of applying radiation, the treatment is stopped in a stop step 516.

Figure 6:
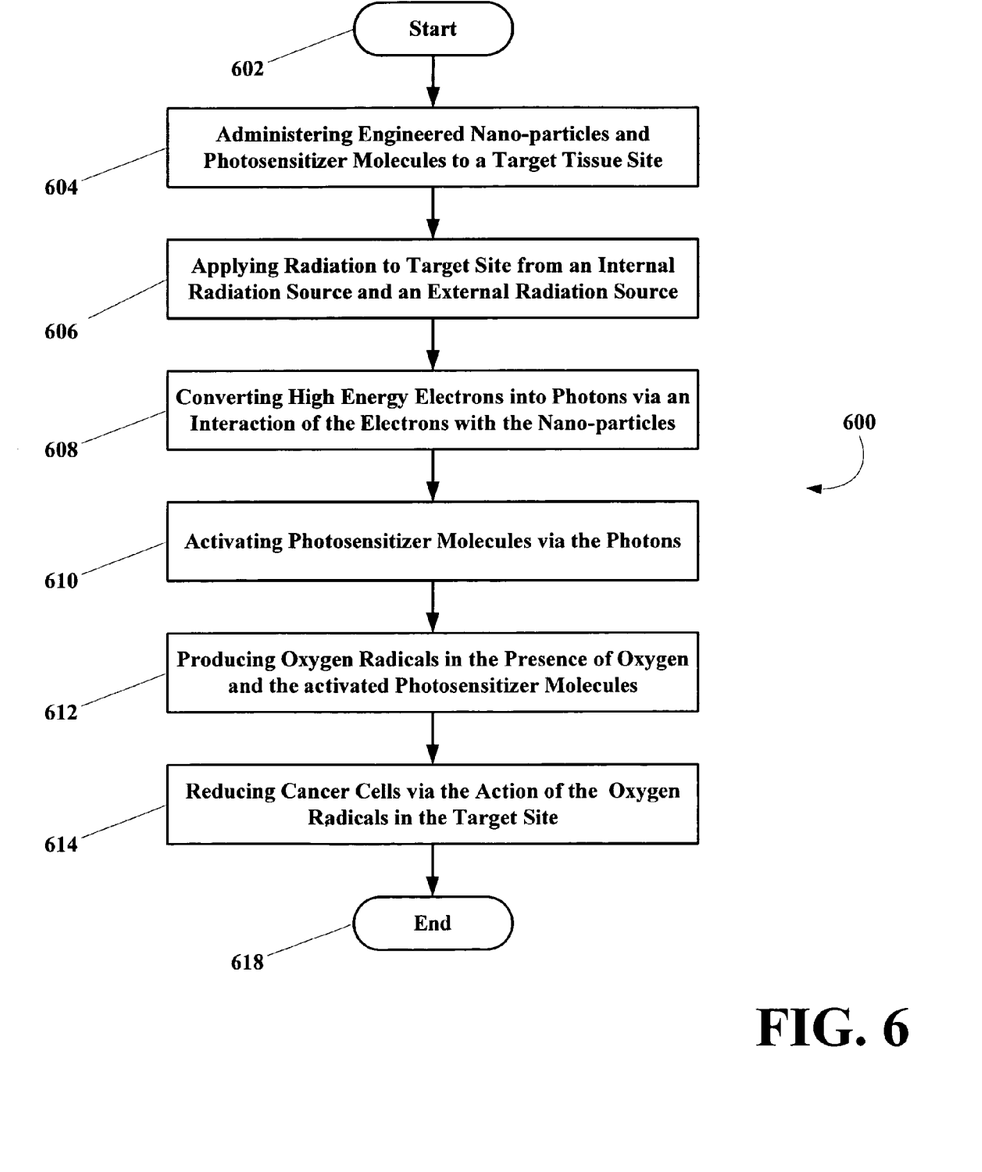
FIG. 6 depicts a flow chart of a generalized radiation embodiment of a method of the invention for radiation induced photo-dynamic treatment or radiation and radiation induced photo-dynamic treatment with internal and external radiation sources of a tissue site.

Referring now to FIG. 6, a flow chart, generally 600, illustrates of an combined radiation embodiment of a method of the present invention, where the method include two radiation sources: an external radiation source and an implantable radiation sources including $^{103}$Pd radio-seeds, implanted $^{125}$I radio-seeds or any other radio isotope capable of being formed into radio-seeds. The method begins with a start step 602. The start step 602 is simply a flow chart convenience in actuality the method actually begins with the first step involving the treatment. However, the start step 602 does mean that the medical team has assembly and has the necessary amount of nano-particles having a desired bandgap for converting energized electronic into photons having an energy sufficient to excite corresponding photosensitizer molecules. Once the team and materials are ready, the nano-particles and photosensitizer molecules are administered to a target tissue site in administering step 604. The administering step 604 can be any known or yet to be invented administering step that is capable of localizing an effective amount of the nano-particles and the photosensitizer in the target site, e.g., injection into the blood stream with affinity agents to aid in localization, direct injection into the tissue site and/or surrounding region, direct profusion into the tissue site and/or surrounding, or any other administering step that is capable of localizing an effective amount of both the nano-particles and the photosensitizer in the target site. The tissue site can be a tumor and/or the tumor and surrounding tissue, a non-tumor cancerous growth or any other tissue site include cells that require eradication via radiation or oxygen radicals induced by light activated photosensitizers. After the nano-particles and photosensitizer molecules (whether individually, collectively, or in an associated format) is administered and effective amount of the nano-particles and photosensitizer molecules are present in the tissue site, radiation is applied to the tissue site in an applying radiation step 606, which in this case includes an administering step where the internal radiation source (radio-seeds) are implanted in the tissue site along with the nano-particles and the photosensitizer. Moreover, the three materials can be simultaneously administered so that in a single administering step all three components are introduced into the site. As the radiation is applied to the tissue site from an internal radiation source and an external radiation source during the applying radiation step 606, a portion of the radiation produces energized electrons such as photoelectrons, Compton electrons, or the like, are absorbed by the nano-particles and converted into photons having a desired frequency range in a converting step 608. After conversion, the photon are absorbed by the photosensitizer molecules forming activated photosensitizer molecules in an activating photosensitizer step 610. The activated photosensitizer molecules in the presence of oxygen in the tissue site produces oxygen radicals in a producing oxygen radicals step 612. The produced oxygen radicals then interact with the cells of the tissue site resulting in cell death or a reduction or elimination of a tumor in a reducing cancer cells step 614. After a desired duration of applying radiation, the treatment is stopped in a stop step 616.

In the above embodiments, the radiation applied to the tumor can be from traditional radiation sources include, without limitation, gamma ray or X-rays of 0.02 to 50 MeV sources, $^{125}$I radioactive seeds and $^{103}$Pd radioactive seeds. The high energy electrons produced by the radiation are converted to photons of about 630 nm (or 2 eV) by the nano-particles, especially semiconductor nano-particles. The photosensitizer molecules are activated by the 630-nm photons and, in the presence of oxygen, produce oxygen radicals that kill the selected tumor.

One embodiment of the present invention for treatment of prostate cancer, as described above, is innovative on multiple fronts, as described below:

(1) The present invention modifies an approved radiation procedure to incorporate the PDT paradigm, assuring compatibility with existing technology. No additional intervention is required besides injection of Photofrin.

(2) Using semiconductor nano-particles to generate the light emission needed for PDT allows the extension of this form of treatment to regions of the body that are inaccessible with standard PDT methods.

(3) The treatment time of radiation-based methods (e.g., the lifetime of a brachytherapy implant using $^{125}$I is $1.44*\tau_{1/2}=1.44*60=86.4$ days, or multiple sessions lasting few minutes each for external beam treatments) is well within the range of strong activity of Photofrin inside the body. This allows for maximum synergy during the treatments.

(4) The same platform used for radiation treatment planning can be used for PDT modeling.

(5) In addition to the spatiotemporal synergy described above, the two modalities provide for significant biological synergy. The free radicals created by PDT may "fix" the DNA double-strand breaks induced by radiation (the sentinel event that leads to tumor cell-kill), thus preventing repair.

(6) The combined radiation/photodynamic therapy treatment modality of the present invention is a one step procedure with the following advantages:

(a) The combined treatments can be performed without additional burden to the patient;

(b) The cure rates can be similar to radiation at lower radiation doses and thus reduced toxicity, which can be important for early-stage cancer patients and can improve quality of life; and (c) The cure rates can be higher than either radiation or PDT alone with no increased toxicity, which can be more important for patients with higher-risk disease.

(7) The use of low dose rate PDT over extended periods has been shown in preliminary studies of cell cultures to be effective at killing tumor cells. See Stuart K. Bisland, Lothar Lilge, Annie Lin, Robert Rusnov, and Brian C.

Wilson. "Metronomic Photodynamic Therapy as a New Paradigm for Photodynamic Therapy: Rationale and Preclinical Evaluation of Technical Feasibility for Treating Malignant Brain Tumors", Photochemistry and Photobiology 80, p. 22-30 (2004). This is important because damage to normal cell tissues at the lower dose rates can potentially be minimized.

(8) Nano-materials and devices with optical emission (low energy) and absorption (high energy) characteristics can be tuned to maximize the photosynthesizer activity and significantly enhance the local radiation dose.

One embodiment described here is also applicable to treatment of other types of cancer and to treatment wherever photoenhanced (non-cancer) therapies are desirable but difficult to implement.

The present invention can be used in many existing and future applications. The following applications are meant by way of example and are not meant to limit the scope of the invention:

(1) Treatment of cancers, which are currently or potentially treatable by radiation-based means, such as, without limitation, oesophageal cancers, lung cancers, head cancers, neck cancers, bladder cancers, brain cancers, skin cancers, prostate cancers, and breast cancers.

(2) Treatment of cancers, which are currently or potentially treatable by photodynamic-based means, such as, without limitation, oesophageal cancers, lung cancers, head cancers, neck cancers, bladder cancers, brain cancers, skin cancers, prostate cancers, and breast cancers.

(3) Photosensitizers operating in any spectral range, inclusive of those currently available and those under development, including, without limitation, PHOTOFRIN® (a registered trademark of Axcan Pharma Inc., Birmingham, Ala.), LEVULAN® (a registered trademark of DUSA Pharmaceuticals, Inc., Wilmington, Mass.), PHOTREX® (rostaporfin, SnET2) (a registered trademark of Mallinckrodt Baker, Inc., St. Louis, Mo.), FOSCAN® (a registered trademark of Biolitec Pharma Ltd, Dublin, Ireland), Verteporfin, LUTRIN® (a registered trademark of Pharmacyclics, Inc., Sunnyvale Calif.), NPe6 (mono-L-aspartyl chlorin e6) and any other photosensizer currently capable of converting photons into photon effective for PDT therapy.

(4) Photo-dynamic treatments using photosensitizers in any from, such as solids, liquid, gaseous, or nano-materials.

(5) Novel uses of photo-dynamic therapy such as UV irradiation for bacterial and viral destruction for drug resistant strains.

(6) Other applications where remote generation of a photon flux might enable the use of traditional yet powerful probes; i.e., non destructive testing (NDT) methods where radiation is used to generate photons at selected depths within a solid material thus enabling measuring/mapping of various parameters using fluorescence or other methods. Similarly photons can be generated wirelessly deep within transparent, translucent, partially opaque or opaque. The light emitting nano-particles are especially well suited for translucent, partially opaque and opaque structures where standard photolytic means would not represent a viable method for introducing photons into the structures. These photons can then be utilized to probe the characteristics of the medium and/or power embedded devices to transmit the collected information.

All references cited herein are incorporated by reference. Although the invention has been disclosed with reference to its embodiments, from reading this description those of skill in the art may appreciate changes and modification that may be made which do not depart from the scope and spirit of the invention as described above and claimed hereafter.

We claim:

1. A method for treating tumors in animals, including humans, by photo-dynamic therapy comprising the step of:
administering an effective amount of nano-particles to a target site of an animal, where the target site includes a cancerous growth and/or tumor,
administering a photo effective amount of a photosensitizer molecule to the target site, and
applying ionizing radiation from a radiation source to the target site,
where the two administering steps can be performed collectively or separately, where the nano-particles are independent of the photosensitizer, where the ionizing radiation has an energy sufficient to generate energetic electrons in the target site, where the nano-particles are capable of absorbing a portion of the generated electrons in a cathodoluminescence process and have a bandgap value sufficient to convert a portion of the absorbed electrons into photons having a frequency range corresponding to an absorption frequency range of the photosensitizer molecules, and where the photosensitizer molecules absorb a portion of the photons activating oxygen to form oxygen radicals capable of producing a localized photodynamic therapeutic affect reducing a number of cancer cells or reducing a size of the tumor.

2. The method of claim 1, wherein the animal is a human and the cancer or tumor is selected from the group consisting of carcinomas, melanomas, lymphomas, plasmocytoma, sarcoma, glioma, thymoma, brain tumor, myeloma, leukemia, or a tumor of pharynx, bones, joints, soft tissue, skin, breast, eye, orbit, the nervous system, endocrine system, urinary system, genital system, respiratory system, digestive system, oral cavity and/or combinations thereof.

3. The method of claim 1, wherein the nano-particles comprise semiconductor nano-particles.

4. The method of claim 3, wherein the semiconductor nano-particles comprise binary compounds from Groups II-VI or Groups III-V, ternary compounds from Groups II-VI or Groups III-V, quaternary compounds from Groups II-VI or Groups III-V, or mixtures or combinations thereof.

5. The method of claim 4, wherein the nano-particles are doped with transition metals selected from the group consisting of Groups IB, IIB, IIIB, IVB, VB, VIB, VIIB, VIII transition metals and mixtures thereof.

6. The method of claim 4, wherein the semiconductor nano-particles comprise a single core compound, a single core compound and a different second outer (shell) compound or mixtures or combinations thereof.

7. The method of claim 6, wherein the semiconductor nano-particles further comprise a non-semiconductor surface layer material, where the surface layer material comprises silicon dioxide, or a molecule comprising a sulfur, phosphorous, or amine group, or a molecule selected from the group consisting of a synthetic polymer, a peptide or polypeptide, an antibody or a fragment thereof, a nucleic acid, a carbohydrate molecule, a lipid molecule, a drug, or synthetic molecule or mixtures or combinations thereof.

8. The method of claim 1, wherein the semiconductor nano-particles further include a targeting molecule, wherein the targeting molecule binds specifically to molecules localized within the tumor, where the targeting molecule is a peptide or an antibody or the targeting molecule binds specifically to angiogenic molecules in the endothelium of the tumor.

9. The method of claim 1, wherein the nano-particle administering step is by implanting a device containing the nano-particles, injecting the nano-particles directly into the target site, injecting the nano-particles into a body cavity, injecting the nano-particles intravenously, injecting the nano-particles intra-arterially, or a combination of these administering steps.

10. The method of claim 1, wherein the radiation is in a form selected from x-rays having a frequency range between about 1 keV to 50,000 keV, microbeam arrays of x-rays, radioisotopes, electrons, protons, ion beams, or neutrons.

11. The method of claim 1, wherein the two administering steps are performed separately, in either order.

12. The method of claim 1, wherein the radiation source comprise radioactive seeds disposed in the target site.

* * * * *